United States Patent
Husemann et al.

(10) Patent No.: US 10,619,128 B2
(45) Date of Patent: Apr. 14, 2020

(54) CONTAINER WITH A FLEXIBLE WALL

(71) Applicant: Sartorius Stedim Biotech GmbH, Goettingen (DE)

(72) Inventors: Bernward Husemann, Goettingen (DE); Gerhard Greller, Goettingen (DE); Wolfgang Kahlert, Koerle (DE); Heinz-Ruediger Keitel, Melsungen (DE); Davy de Wilde, Spirmont (BE)

(73) Assignee: SARTORIUS STEDIM BIOTECH GMBH (DE)

( * ) Notice: Subject to any disclaimer, the term of this patent is extended or adjusted under 35 U.S.C. 154(b) by 402 days.

(21) Appl. No.: 14/917,626

(22) PCT Filed: Aug. 18, 2014

(86) PCT No.: PCT/EP2014/067582
§ 371 (c)(1),
(2) Date: Mar. 9, 2016

(87) PCT Pub. No.: WO2015/032612
PCT Pub. Date: Mar. 12, 2015

(65) Prior Publication Data
US 2016/0215247 A1 Jul. 28, 2016

(30) Foreign Application Priority Data
Sep. 9, 2013 (DE) .................. 10 2013 109 819

(51) Int. Cl.
*C12M 1/00* (2006.01)
*C12M 1/12* (2006.01)
*C12M 1/26* (2006.01)

(52) U.S. Cl.
CPC ............ *C12M 23/26* (2013.01); *C12M 23/14* (2013.01); *C12M 23/28* (2013.01); *C12M 23/40* (2013.01);
(Continued)

(58) Field of Classification Search
CPC ...................................................... C12M 23/26
(Continued)

(56) References Cited

U.S. PATENT DOCUMENTS

2002/0015671 A1 2/2002 Lee
2005/0287660 A1* 12/2005 Aubry .................... C12M 21/06
435/297.1

(Continued)

FOREIGN PATENT DOCUMENTS

DE 10 2006 014 495 10/2007
DE 10 2008 010 42 8/2009
(Continued)

OTHER PUBLICATIONS ntemational Search Report. X.
International Preliminary Report on Patentability dated Mar. 15, 2016.

*Primary Examiner* — Kevin Joyner
*Assistant Examiner* — Holly Kipouros
(74) *Attorney, Agent, or Firm* — Gerald E. Hespos; Michael J. Porco; Matthew T. Hespos

(57) ABSTRACT

A container (1) has a flexible wall (2) and at least one emptying tube (4, 4', 4") that projects through a wall aperture (7) into the container interior (3) surrounded by the flexible wall (2). The free end (12) of the emptying tube has an emptying opening (13) that can be set in position vertically to different emptying heights (14). The container (1) is distinguished in that an adapter piece (8), in which the emptying tube (4, 4', 4") is held in a longitudinally displaceable manner, is arranged in the wall aperture and in that a portion of the emptying tube (4, 4', 4") is surrounded by a flexible sheath (5) that is connected at a first end (11) to the emptying tube (4, 4', 4") and at its second end (10), which is remote from the first end (11), to the wall (2) or the adapter piece (8).

10 Claims, 5 Drawing Sheets

(52) U.S. Cl.
CPC ............ *C12M 33/00* (2013.01); *C12M 37/02* (2013.01); *C12M 37/04* (2013.01)

(58) Field of Classification Search
USPC ........................................................ 435/289.1
See application file for complete search history.

(56) References Cited

U.S. PATENT DOCUMENTS

| | | |
|---|---|---|
| 2007/0227270 A1 | 10/2007 | Mennenga et al. |
| 2010/0112700 A1* | 5/2010 | Shaaltiel ................ C12M 23/26 435/410 |
| 2011/0003374 A1 | 1/2011 | Van Den Boogaard et al. |
| 2011/0038222 A1 | 2/2011 | Ludwig et al. |
| 2012/0077243 A1 | 3/2012 | Niazi |
| 2012/0097557 A1 | 4/2012 | Baumfalk et al. |
| 2012/0309076 A1* | 12/2012 | White ................... C12M 23/14 435/255.1 |
| 2013/0071872 A1* | 3/2013 | Ho ......................... C12M 33/04 435/29 |
| 2013/0170315 A1 | 7/2013 | Martens |
| 2016/0040109 A1 | 2/2016 | Dahlberg et al. |
| 2016/0194591 A1* | 7/2016 | Castan ................... C12M 23/14 435/348 |

FOREIGN PATENT DOCUMENTS

| | | |
|---|---|---|
| DE | 10 2009 037 345 | 12/2010 |
| DE | 20 2012 005 989 | 8/2012 |
| GB | 829713 | * 2/1960 |
| NO | 2011/082787 | 7/2011 |
| NO | 2011/094534 | 8/2011 |
| WO | 2007/044047 | 4/2007 |
| WO | 2007/134267 | 11/2007 |
| WO | 2009/122310 | 10/2009 |

* cited by examiner

CONTAINER WITH A FLEXIBLE WALL

BACKGROUND

1. Field of the Invention

The invention relates to a container with a flexible wall and with at least one emptying tube that projects through a wall aperture into the container interior surrounded by the flexible wall, the free end of which emptying tube has an emptying opening that can be set in its position in the vertical direction to different emptying heights.

2. Description of the Related Art

WO 2011/094534 A2 discloses a container with a flexible wall that has a container interior into which the free end of an emptying tube projects through a wall aperture. The free end of the emptying tube has an emptying opening that is adjustable to different emptying heights.

In this regard, it is disadvantageous that the emptying tube projects into the container interior through a rotation adapter arranged within a wall aperture on a side wall and that it is necessary for the free end to be angled at 90° within the container interior. The emptying tube is arranged so as to be rotatable within the rotation adapter, which allows the emptying height to be adjusted by means of a rotation. If the container is designed as a cylinder and the angled free end of the emptying tube is placed close to the wall, it can come into contact with the wall, thereby preventing it from rotating 360°. When installed proximate to the middle of the container, the free end can come into contact with a stirrer located in the middle of the container. It is also disadvantageous that the emptying tube, which is arranged so as to be rotatable within the adapter, is very difficult to seal. Because of the relatively high costs associated with this, the disclosed container is therefore not suitable as a cost-effective single-use container.

The present invention seeks to solve the problem of providing a container with a flexible wall, having an emptying tube, whereby the emptying opening is to be adjustable to different emptying heights. With regard to the container, the emptying tube is therefore to be designed to be secure and cost-effective, such that the container, in particular, is suitable for use as a single-use container.

SUMMARY

This problem is solved by a container with a flexible wall and with at least one emptying tube that projects through a wall aperture into the container interior surrounded by the flexible wall. The free end of the emptying tube has an emptying opening that can be set in its position in the vertical direction to different emptying heights. The container is characterized in that an adapter piece, in which the emptying tube is held in a longitudinally displaceable manner, is arranged in the wall aperture and in that a portion of the emptying tube is surrounded by a flexible sheath which is connected at a first end to the emptying tube and at its second end, which is remote from the first end, to the wall or the adapter piece.

The flexible sheath with the second end that makes a sealed connection to the wall of the flexible container or to the adapter piece, and with the second end that makes a sealed connection with the emptying tube, ensures straightforward and secure sealing without contamination risk. The flexible sheath forms a sterile barrier. The secure sealing provided by the flexible sheath makes it relatively easy, such as by means of O ring seals, to position the emptying tube in the adapter piece in such a manner that the emptying tube remains displaceable and fastened. The adapter piece can therefore also be designed in a straightforward and cost-effective manner. In particular, this makes the container suitable as a cost-effective and secure single-use container. The emptying tube that projects into the container interior can project into the container interior vertically, from above, or diagonally, from the side, for example.

Instead of the flexible sheath, O ring seals or similar sealing elements can also be used, especially those suitable for use in glass or stainless steel containers.

According to one embodiment of the invention, the flexible sheath is designed as a hose or tubular film. This forms an especially cost-effective sterile barrier. The flexible sheath can also be designed as a bellows hose.

According to another embodiment of the invention, the flexible sheath is arranged within the container interior. The arrangement within the container interior makes it possible to employ a relatively thin sheath design since within the container interior it is protected by the container walls.

The emptying tube may be designed as an extensible telescopic tube. This also enables drainage proximate to the container base. However, it is also possible to design the emptying tube as a flexible hose.

One or more hose guides to guide the free end of the emptying tube may be arranged on the wall within the container interior. The hose guide prevents the flexible hose from being laterally displaced, such as by flow dynamics caused by a stirrer.

According to another embodiment, a filter, such as a depth filter, is placed upstream of the emptying opening. This allows for retention of specific particles.

The end of the emptying tube facing away from the emptying opening may have one part of a sterile connector. It is also possible to replace the aforementioned sterile connector with a weldable hose for sterile connection of two hoses.

A second emptying tube may project into the container interior. The second emptying tube can be arranged on the opposite side of the container interior from the first emptying tube.

The container with emptying tube may be employed as a single-use container.

Additional features and advantages of the invention are evident from the following special description and the drawings.

DETAILED DESCRIPTION

Figure 1:
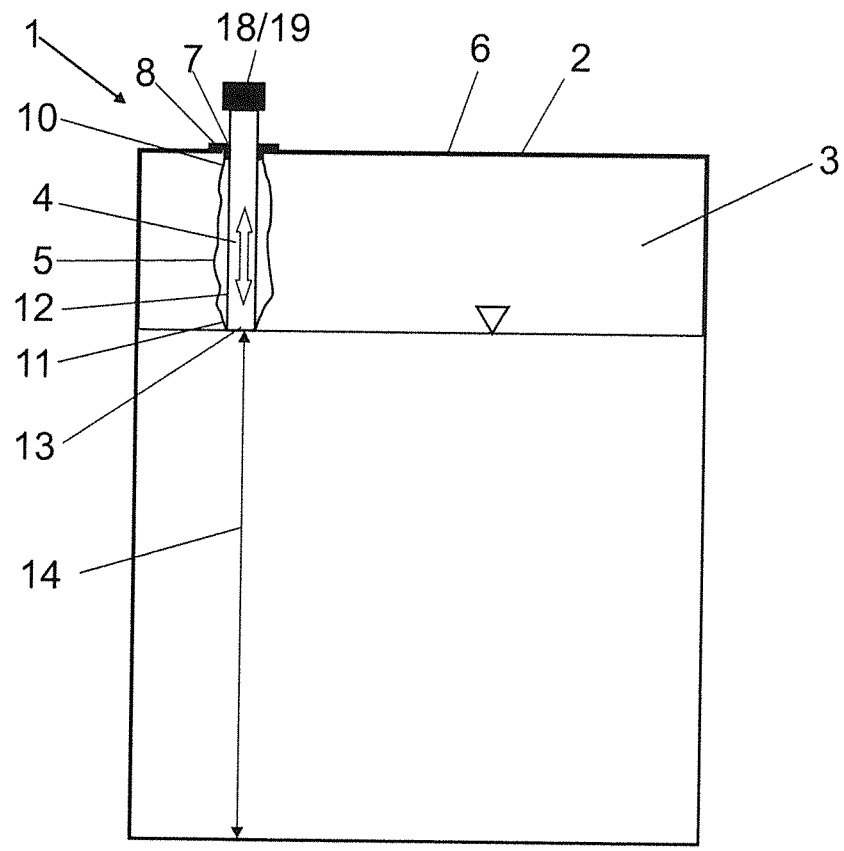
FIG. 1 is a schematic lateral view of a container with a flexible wall, having a height-adjustable emptying tube with a flexible sheath
Figure 1A:
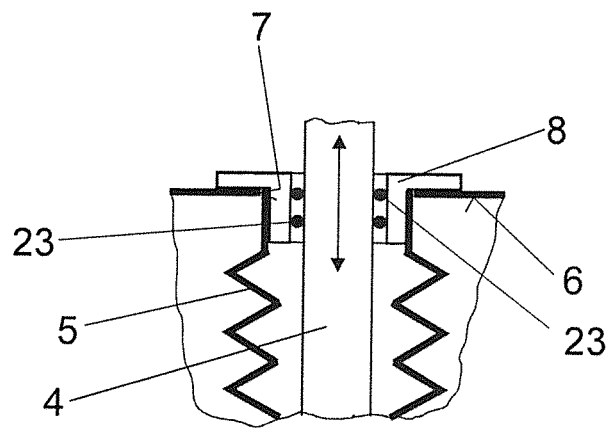
FIG. 1a is a schematic lateral view of a region where the height-adjustable emptying tube enters the container.

A container 1 with a flexible wall 2, such as for a bioreactor, essentially consisting of a container interior 3, an emptying tube 4 and a flexible sheath 5.

According to the exemplary embodiment from FIG. 1, the container 1 has a top 6 arranged in vertical direction with a wall aperture 7 within which the emptying tube 4, which projects into the container interior 3, is arranged in a longitudinally displaceable manner. The emptying tube 4 can be guided within the adapter piece 8 using sealing rings 23. The second end 10 of the flexible sheath 5 is connected to the adapter piece 8 in a fluid-tight manner, such as by welding. The first end 11 of the flexible sheath 5, which faces away from the second end 10, is connected to the free end 12 of the emptying tube 4 in a fluid-tight manner, such as by welding. The free end 12 of the emptying tube 4 has an emptying opening 13 whose respective position is determined by the variable emptying height 14.

Figure 2:
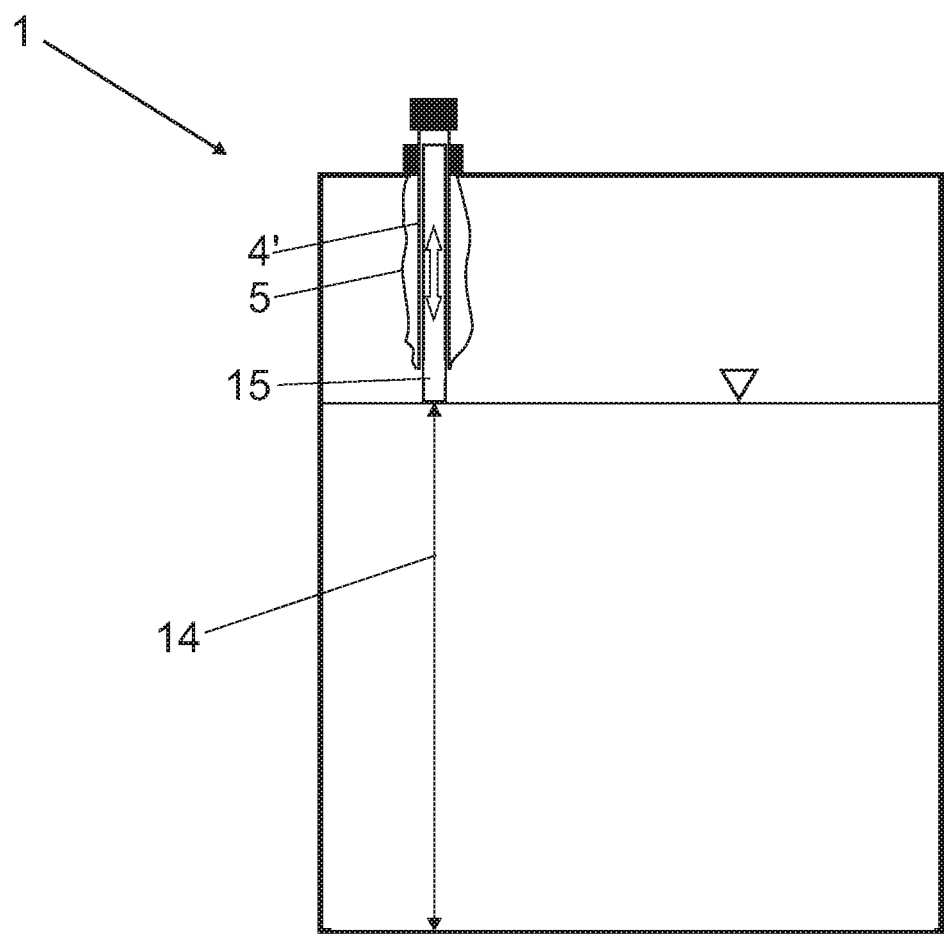
FIG. 2 is a schematic lateral cross-section of another container with a flexible wall, having an emptying tube designed as an extensible telescopic tube with a flexible sheath.

According to the exemplary embodiment from FIG. 2, the emptying tube 4' is designed as an extensible telescopic tube. The emptying tube 4' has a second extensible or retractable tube 15.

Figure 3:
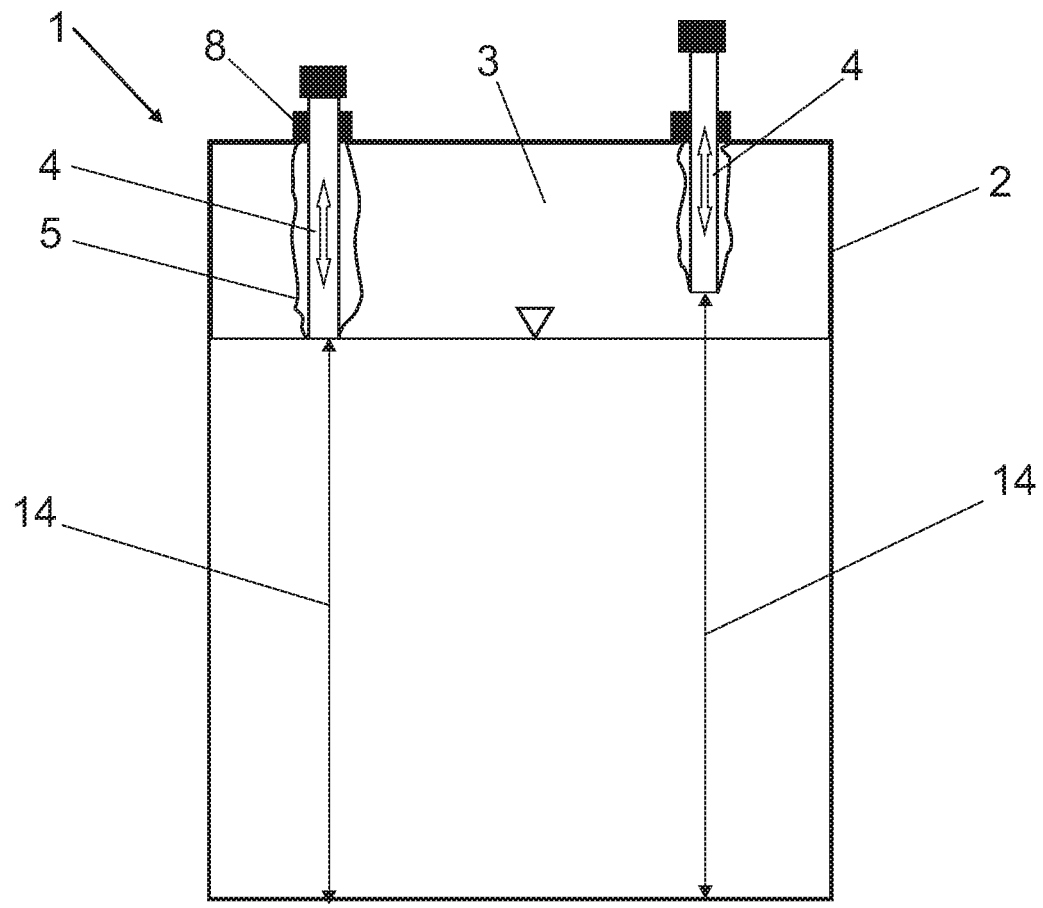
FIG. 3 is a lateral cross-section of another container with a flexible wall, having two emptying tubes, each with a flexible sheath.

According to the exemplary embodiment from FIG. 3, the container 1 has a second emptying tube 4 on the top 6, in addition to the first emptying tube 4. The second emptying tube 4 can also be arranged near the container base 16 that faces away from the container top 6, such that the second emptying tube 4 is arranged on the opposite side of the container interior 3 from the first emptying tube 4.

Figure 4:
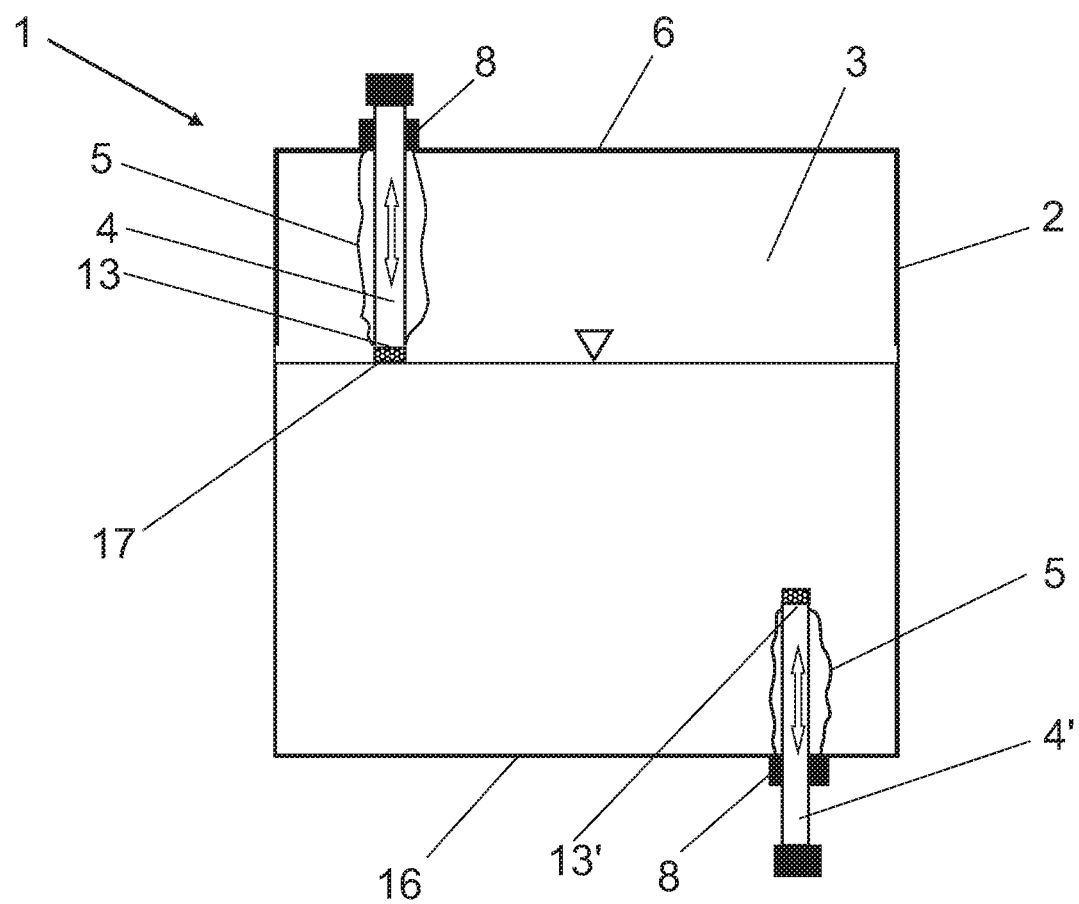
FIG. 4 is a lateral cross-section of another container with a flexible wall, having, in addition to a first emptying tube with flexible sheath arranged near the top of the container, a second emptying tube with flexible sheath arranged near the base of the container.

According to the exemplary embodiment from FIG. 4, a filter 17 can be arranged upstream from each of the emptying tubes 4, 4' at the free ends 12 of their emptying openings 13, 13'.

Figure 6:
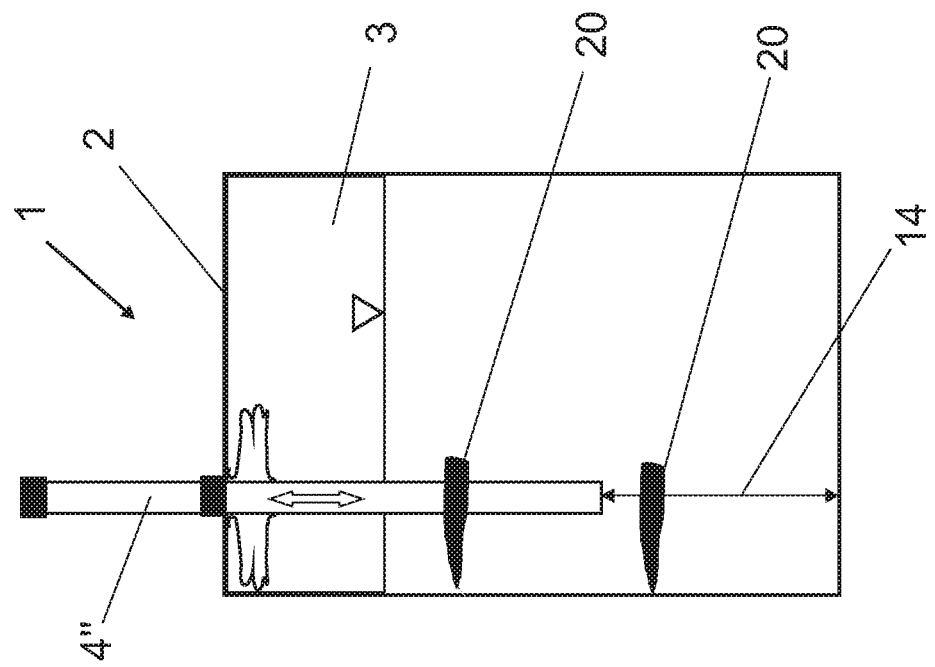
FIG. 6 is a lateral cross-section of the container from FIG. 6 with a partially extended emptying tube.
Figure 5:
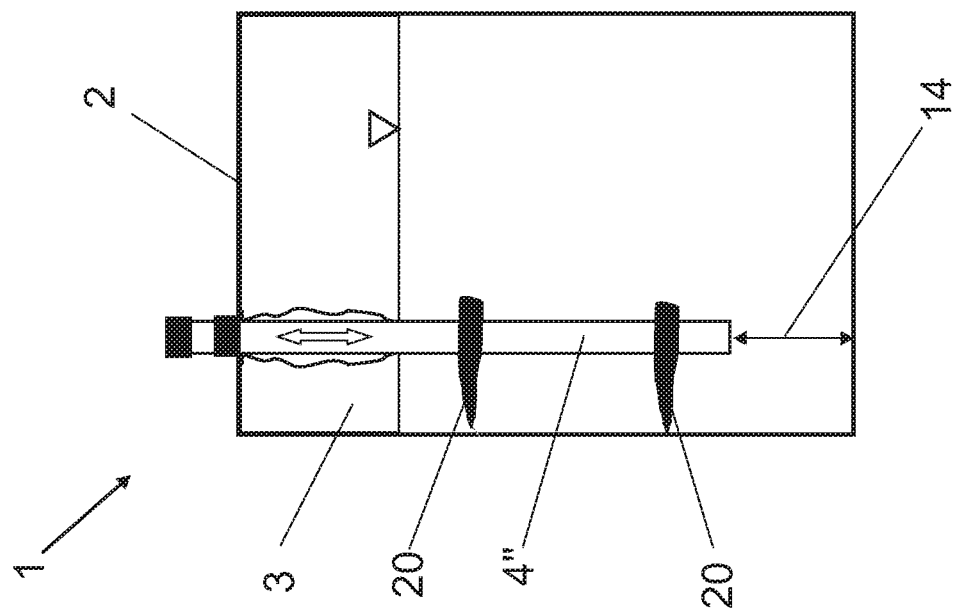
FIG. 5 is a lateral view of another container with a flexible wall, having an emptying tube, designed as a flexible hose, with a flexible sheath, arranged in the upper partial region of the emptying tube and with hose guides arranged on the wall of the container.

According to the exemplary embodiments in FIGS. 5 and 6, the emptying tube 4" can be designed as a flexible hose, whereby two hose guides 20 are arranged on the wall 2 within the container interior 3 in order to guide the free end of the emptying tube 4". The flexible sheath 5 is designed as a relatively thin hose or an encasing tubular film. The sheath 5 can also be designed as a bellows hose.

The container 1 is intended to be employed as a single-use container and, in particular, can be used as a container with a flexible wall for a bioreactor (not shown).

The end of the emptying tube 4 facing away from the emptying opening 13 has a first part 18 of a two-part sterile connector 19.

Of course, the embodiments discussed in the specific description and shown in the figures are merely illustrative exemplary embodiments of the present invention. In light of this disclosure, a person skilled in the art is given a wide range of possible variations.

LIST OF REFERENCE NUMBERS

1 Container
2 Flexible wall
3 Container interior
4, 4', 4" Emptying tube
5 Flexible sheath
6 Top of 1
7 Wall aperture
8 Adapter piece
10 Second end of 5
11 First end of 5
12 Free end of 4
13, 13' Emptying opening
14 Emptying height
15 Second tube of 4'
16 Base of 1
17 Filter
18 First part of 19
19 Sterile connector
20 Hose guide

The invention claimed is:

1. A container (1) comprising:
a flexible wall (2) that includes a top wall (6) of the container (1), the top wall (6) being formed with a wall aperture (7);
an adapter piece (8) held in the wall aperture (7) in the top wall (6);
an emptying tube (4, 4', 4") that projects through the wall aperture (7) in the top wall (6) and into a container interior (3) surrounded by the flexible wall (2), the emptying tube (4, 4', 4") having a free inner end (12) with an emptying opening (13) within the container interior (3), an outer end above the top wall (6) and an intermediate portion longitudinally displaceable in the adapter piece (8) so the free end (12) with the emptying opening (13) can be set selectively in the vertical direction to different emptying heights (14);
a filter (17) arranged at the free inner end (12) of the emptying tube (4, 4', 4") and at a position upstream from the emptying opening (13), the filter (17) allowing for retention of specific particles as the emptying opening (13) is set selectively in the vertical direction to different emptying heights (14);
a flexible sheath (5) arranged within the container interior (3) and surrounding at least a portion of the emptying tube (4, 4', 4"), the flexible sheath (5) having opposite first and second ends (11, 10), the first end (11) being connected to the free inner end (12) of the emptying tube (4, 4', 4") and the second end (10) of the flexible sheath (5) being connected to the top wall (6) or the adapter piece (8) that is held in the wall aperture (7) in the top wall (6); and
sealing rings (23) between the intermediate portion of the emptying tube (4, 4', 4") and the adapter piece (8), the sealing rings (23) guiding the longitudinal displacement of the emptying tube (4, 4', 4") in the adapter piece (8) and providing sealing therebetween.

2. The container of claim 1, wherein the flexible sheath (5) is a hose or tubular film.

3. The container of claim 1, wherein the flexible sheath (5) is a bellows hose.

4. The container of claim 1, wherein the emptying tube (4') is an extensible telescopic tube.

5. The container of claim 1, wherein the emptying tube (4, 4', 4") is a flexible hose.

6. The container of claim 5, further comprising one or more hose guides (20) arranged on the flexible wall (2) within the container interior (3) to guide the free end (12) of the emptying tube (4, 4', 4").

7. The container of claim 1, wherein the outer end of the emptying tube (4, 4', 4") has one part (18) of a sterile connector (19).

8. The container of claim 1, wherein the emptying tube (4, 4', 4") is a first emptying tube (4, 4', 4"), the container further comprising a second emptying tube (4, 4', 4") that projects into the container interior (3).

9. The container of claim 8, wherein the second emptying tube (4, 4', 4") is arranged on an opposite side of the container interior (3) from the first emptying tube (4, 4', 4").

10. The container of claim 1 wherein the container (1) with the emptying tube (4, 4', 4") is employed as a single-use container.

* * * * *